(12) United States Patent
Connery

(10) Patent No.: US 6,761,817 B2
(45) Date of Patent: Jul. 13, 2004

(54) SMART DETERMINATION OF DISSOLVED OXYGEN PROBE OPERATING BIAS

(75) Inventor: James G. Connery, Maple Glen, PA (US)

(73) Assignee: Honeywell International Inc., Morristown, NJ (US)

( * ) Notice: Subject to any disclaimer, the term of this patent is extended or adjusted under 35 U.S.C. 154(b) by 397 days.

(21) Appl. No.: 10/033,822

(22) Filed: Dec. 19, 2001

(65) Prior Publication Data

US 2003/0111358 A1 Jun. 19, 2003

(51) Int. Cl.$^7$ ................................................. G01N 27/40
(52) U.S. Cl. ........................ 205/783; 204/401; 204/415
(58) Field of Search .............................. 205/782, 782.5, 205/783, 785.5; 204/401, 415, 431, 432

(56) References Cited

U.S. PATENT DOCUMENTS

| | | | |
|---|---|---|---|
| 4,076,596 A | | 2/1978 | Connery et al. |
| 4,457,808 A | * | 7/1984 | Taylor et al. ............ 205/782.5 |
| 4,498,039 A | | 2/1985 | Galwey et al. |
| 4,729,824 A | | 3/1988 | Giner |
| 5,098,547 A | * | 3/1992 | Bryan et al. ................ 204/401 |
| 5,423,963 A | * | 6/1995 | Fletcher et al. .......... 205/782.5 |
| 5,466,356 A | | 11/1995 | Schneider et al. |
| 5,532,602 A | | 7/1996 | Wiget |
| 6,428,684 B1 | * | 8/2002 | Warburton .................. 205/775 |
| 6,447,670 B1 | * | 9/2002 | Holmstrom ................. 205/775 |

FOREIGN PATENT DOCUMENTS

DD          148 387 A       5/1981

OTHER PUBLICATIONS

Honeywell Inc., Industrial Automation and Control Division, "The Series 7020 Dissolved Oxygen Analyzer/Controller" Specification 70–82–03–16, dated 1/97, pp. 1–4.

Honeywell Inc., "The Series 7020 dissolved Oxygen Analyzer", User's Manual 70–82–25–66, Rev. 3, dated 2/98, pp. 1–102.

International Search Report, dated Mar. 25, 2003, relative to PCT application No. PCT/US 02/39603, the foreign equivalent to the instant U.S. application 10/033,822.

Vassos, E., "Controlled–Current Methods", Chap 9, Electroanalytical Chemistry, 1983, XP002234013, pp. 140–151, 231–235.

* cited by examiner

Primary Examiner—Kaj K. Olsen
(74) Attorney, Agent, or Firm—Andrew A. Abeyta; Ortiz & Lopez, PLLC

(57) ABSTRACT

A method and system for determining dissolved oxygen is disclosed. One or more constant currents are driven through amperometric-type dissolved oxygen probes to develop reference electrode potentials defining the envelope of oxygen electrochemistry. The reference electrode voltage is generally measured at a first current level and at a second current level utilizing the oxygen probe, wherein the first and second current levels define limitations of oxygen electrochemistry. An optimum electrode bias voltage can thereafter be automatically calculated based the reference electrode voltage measured at the first current level and the second level to thereby provide accurate indications of dissolved oxygen thereof.

32 Claims, 7 Drawing Sheets

SMART DETERMINATION OF DISSOLVED OXYGEN PROBE OPERATING BIAS

TECHNICAL FIELD

The present invention generally relates to electrochemical sensing techniques and devices thereof. The present invention also relates to techniques and devices thereof for measuring the concentration of gases in fluids. The present invention additionally relates to oxygen probes for measuring dissolved oxygen in fluids.

BACKGROUND OF THE INVENTION

The concentration of dissolved oxygen (DO) in water-based systems is important either to assure adequate oxygen level in natural waters or to assure low dissolved oxygen in processes where dissolved oxygen can be expected to be corrosive. Dissolved oxygen is generally measured with an amperometric electrochemical sensor, whose signal is proportional to oxygen partial pressure. Because dissolved oxygen concentration is directly proportional to oxygen partial pressure at constant temperature, with a secondary measurement of water temperature, dissolved oxygen concentration in suitable units of measurement can be readily determined.

In a conventional oxygen probe, a thin gas-permeable membrane is utilized to isolate the water sample and the electrochemical cell. The electrochemical cell consists of at least two electrodes, one of which can be located internal to the thin gas-permeable membrane. This electrode is controlled by suitable means at a relatively negative potential compared to the second electrode. This electrode is often referred to as a cathode. Two or more internal electrodes can be immersed in an ionically conducting electrolyte. In operation, oxygen diffuses through the membrane from the sample side to the cathode, where it is electrochemically reduced to water. Hence, the oxygen partial pressure is zero at the membrane cathode interface and the difference in partial pressure across the membrane determines the oxygen flux. Measurement of probe current is directly proportional to membrane flux and oxygen partial pressure; with temperature measurement, probe current is suitably temperature compensated to allow for dissolved oxygen concentration computation and display.

One implementation of a dissolved oxygen probe is described in U.S. Pat. No. 4,076,596 to Connery et al., which is incorporated herein by reference. Connery et al. describes an apparatus for electrolytically determining a species in a fluid, including a method of use thereof.

Connery et al. generally describe an electrolytic cell for measuring the concentration of a species, such as oxygen. Depositing closed-spaced interleaved inert electrode surfaces on the surface of an insulating substrate and covering the electrode surfaces with a thin film of electrolyte and permeable membrane can construct the electrolytic cell. The electrolyte can be selected so the species being measured is generated at one electrode surface and consumed at the other with no net reaction in the electrolyte. Alternatively, closely winding two thin electrode wires about a cylindrical base and covering it with an electrolyte and a membrane may form a cylindrical configuration.

Dissolved oxygen can thus be measured in a liquid or fluid based on an amperometric sensor or probe in which oxygen gas from a measurement sample initially diffuses through a gas permeable membrane. Oxygen diffuses through the membrane into an electrolyte and is consumed at an electrode by electrochemical reduction to water at a working electrode, often referred to as a cathode. The chemical reaction that takes place can be represented by the following chemical formulation of equation (1):

$$O_2 + 4H^+ + 4e \rightarrow 2H_2O \tag{1}$$

The driving force for oxygen diffusion through the membrane can be calculated by determining the difference in partial pressures across the membrane. In addition to that described in equation (1), a conventional dissolved oxygen ("DO") probe can employ a chemically inert counter electrode, as described in U.S. Pat. No. 4,076,596. Such an oxygen probe, including later applications thereof, employ configurations in which the electrical current results from the reaction of equation (1) above passing through a companion counter electrode (or anode). This current is equal in magnitude to equation (1) but is of the opposite sign; and, hence, the reverse chemical reaction occurs at this counter electrode. The chemical reaction that can occur at this counter electrode can be represented by the following formulation of equation (2):

$$2H_2O \rightarrow O_2 + 4H^+ + 4e \tag{2}$$

It is readily apparent that the sum of equations (1) and (2) does not correspond to any net chemical reaction. Because a net reaction does not result, reagents are not consumed. This method substantially reduces possible contributions of parameters that influence permeability, such as measurement sample stirring and membrane fouling. The electron flow illustrated by equations (1) and (2) above is thus directly proportional to oxygen partial pressure, which in turn is directly proportional to the oxygen concentration.

FIG. 1 depicts a prior art graph 10 illustrating normal dissolved oxygen probe operation at a controlled potential. Graph 10 illustrates half of the electrochemical fingerprint of oxygen dissolved in a conductive electrolyte within the DO probe. Only positive currents, corresponding to electrochemical reduction reactions are generally illustrated in FIG. 1. Because the actual probe current is a function of electrode geometry, current values are not displayed on the Y-axis 12 in graph 10. FIG. 1 indicates that DO can be reduced to water at potentials more negative than approximately −0.1 V and that a potential window exists wherein current is independent of applied voltage. The curve 14 illustrated in FIG. 1 has a characteristic sigmoid shape with a plateau region 16, centered about −0.6 V as indicated by reference numeral 19. This plateau region 16 corresponds to a limitation of reduction current because oxygen consumption is diffusion limited. As indicated at reference numeral 13, limiting current is generally proportional to oxygen partial pressure. Line 17 generally in FIG. 1 generally indicates a lower spec limit, while line 15 generally indicates an upper spec limit.

Because of the current limitation, it should be clear that probe current has little to no dependence on a reference electrode bias voltage as long as the controlled potential is located near the middle of the wave's plateau. At all bias voltages at which oxygen is reducible to water, measured current is generally directly proportional to oxygen partial pressure. At potentials more negative than approximately −0.9 V, sufficient energy is available to electrochemically reduce water to hydrogen gas. The slope 18 of the water reduction is quite steep, reflecting the large relative concentration of water. Thus, no diffusion limiting current is observed, based on graph 10 of FIG. 1.

FIG. 2 illustrates a prior art schematic diagram illustrating a DO probe 20 in controlled potential mode. FIG. 2 thus depicts a simplified representation of DO measurement electronics. A working electrode or cathode 23 of the DO probe 20 is generally connected to a transconductance amplifier 22 in which input voltage is maintained at a signal common potential and the amplifier output 29 is generally proportional to the current. Because node 25 is generally connected to a negative input of amplifier 22, this can result in the formulation $E_o = -R_f I_{in}$ ($\alpha\, pO_2$) at amplifier output 29. Amplifier 22 is generally configured electronically in parallel with a resistor 25, labeled $R_f$ in FIG. 2. The remaining amplifiers 24 and 26 indicated in FIG. 2 are composed of a reference electrode buffer (i.e., amplifier 24) and a control amplifier (i.e., amplifier 26). Amplifier 26 is generally connected to a voltage regulator 27. Amplifier 26 maintains the reference electrode +0.6 V above the signal common potential. Namely, in control, cathode 23 is at −0.6 V compared to the reference electrode voltage, consistent with the current-voltage curves illustrated in FIG. 1. DO probe 20 further includes an anode 28 and a reference electrode 21. The prior art described above thus is capable of accommodating approximately 85% of measurement applications. Inherent to proper sensor function is the assumption that the current-voltage characteristics are as shown in FIG. 1.

There are two major exceptions, both related to specific applications, in which current-voltage curves significantly deviate from those illustrated in FIG. 1. The first exception is for those applications in which the reference electrode electromagnetic frequency (EMF) significantly changes. This can occur in applications containing sulfides and mercaptans. Because sulfides and mercaptans are gases with water solubility, these compounds are capable of diffusing through the gas permeable electrode membrane. Once inside the DO probe, these specific compounds will react with the silver ion from the probe's reference electrode and precipitate because of their significantly lower solubility. The corresponding reduction of silver ions results in an approximate −60 mV shift for each decade reduction in active silver. Reference EMF shifts of −0.3 V to −0.6 V are common.

FIG. 3 depicts a prior art graph 30 illustrating DO probe operation at a controlled potential with −0.4 V reference electrode EMF shift. Graph 30 of FIG. 3 generally illustrates the normal current-voltage curve, along with a −0.4 V reference shifted (dotted) curve 32. On close examination of graph 30, it can be seen that the curve 32 contains the same information about measurement sample DO content. The oxygen and water reduction potentials, however, are shifted. While curve 32 contains the same information, current measurement at −0.6 V can lead to serious errors. A failure to recognize the bias shift could lead the user to conclude that the DO probe is shorted, or the user might attempt to recalibrate the DO probe/analyzer only to find that the DO probe output is no longer directly proportional to dissolved oxygen. In FIG. 3, a current out-of-range value is indicated at reference numeral 33. Additionally a normal current value is indicated by reference numeral 35.

A second class of applications includes those involving acid gases, such as DO measurement in pressurized carbonated beverages. For example, carbon dioxide is a water-soluble gas, which is readily permeable through the probe membrane. Once inside, $CO_2$ is not electrochemically active per se but does reduce the electrolyte pH. Because hydrogen ion is a reactant in the water reduction, as illustrated in FIG. 1, greater acidity decreases the external energy input requirements by approximately 60 mV/pH.

FIG. 4 illustrates a prior art graph 40 illustrating DO probe operation at a controlled potential with a −5 pH electrolyte pH shift. Graph 40 of FIG. 4 generally illustrates the before and after current-voltage curves for a 5 pH acid shift. It should be noted that the leading edge of the oxygen reduction wave does not move, that water reduction commences at more positive potentials, and that the extent of the plateau is shrunk. A normal current reading is indicated by reference numeral 43 in FIG. 4. It should be further noted that absent any corrective action, higher current readings (i.e., see reference numeral 41) can be observed leading to measurement problems analogous to the reference shift described earlier.

Current-voltage shifts are known. An example of a conventional approach to address problems inherent with current-voltage shifts is employed in the Honeywell 7020 analyzer. This dedicated DO instrument has the capability of performing a current-voltage scan and displaying results, as indicated in FIGS. 1, 3 and 4 herein on an LCD dot matrix display. Approximately three minutes can be required to scan and display the current-voltage curve. It is then up to the operator to evaluate the displayed results and to select a new operating bias voltage. Thus, to overcome such application deficiencies of reference electrodes in DO probes, a need exists for an automated approach to determining dissolved oxygen bias voltage. A fully automated method and device thereof is not known to exist today. The present inventor thus believes that the present invention disclosed herein meets this important need.

BRIEF SUMMARY OF THE INVENTION

The following summary of the invention is provided to facilitate an understanding of some of the innovative features unique to the present invention, and is not intended to be a full description. A full appreciation of the various aspects of the invention can be gained by taking the entire specification, claims, drawings, and abstract as a whole.

It is, therefore, one aspect of the present invention to provide an improved electrochemical sensing method and system.

It is, therefore, another aspect of the present invention to provide an improved method and system for measuring the concentration of gases in fluids.

It is still another aspect of the present invention to provide an improved method and system for measuring oxygen dissolved in fluids.

It is yet another aspect of the present invention to provide an improved dissolved oxygen (DO) probe.

The above and other aspects can be achieved as is now described. A method and system for determining dissolved oxygen is disclosed herein. Instead of determining cathode current at controlled potential, it is possible to control cathode current and measure the corresponding reference electrode voltage. The reference electrode voltage is generally measured at a first current level and at a second current level utilizing the oxygen probe, wherein the first and second current levels define limitations of oxygen electrochemistry. An optimum electrode bias voltage can thereafter be automatically calculated based on the reference electrode voltage measured at the first current level and the second level to thereby provide accurate indications of dissolved oxygen thereof. Thus, one or more constant currents can be driven through amperometric type dissolved oxygen probes to develop reference electrode potentials defining the envelope of oxygen electrochemistry.

The oxygen probe can be configured to include at least one amplifier, which provides a constant current source sufficient to place the oxygen probe in the constant current mode. The amplifier can be, for example, a transconductance amplifier. The oxygen probe can be additionally configured to include at least two resistors electrically in parallel with another. At least one of the resistors is in electrical contact with an amplifier. The other of the two resistors can coupled to a cathode. The output of the amplifier can be connected to an anode. At least one input of an amplifier can be connected to a reference electrode. The cathode generally comprises a working electrode.

The oxygen probe disclosed herein is directed generally to a dissolved oxygen (DO) probe for measuring oxygen dissolved in a liquid. The present invention thus addresses problems associated with the momentary operation of an oxygen probe in a constant current mode, as opposed to a normal constant voltage mode. The reference electrode voltage is measured at two current levels, which define the limits of the oxygen electrochemistry. An optimum electrode bias can then be calculated and electronics associated with oxygen probe configured for normal DO measurement in a constant voltage mode.

BRIEF DESCRIPTION OF THE DRAWINGS

The accompanying figures, in which like reference numerals refer to identical or functionally-similar elements throughout the separate views and which are incorporated in and form part of the specification, further illustrate the present invention and, together with the detailed description of the invention, serve to explain the principles of the present invention.

DETAILED DESCRIPTION OF THE INVENTION

The particular values and configurations discussed in these non-limiting examples can be varied and are cited merely to illustrate an embodiment of the present invention and are not intended to limit the scope of the invention.

The present invention generally discloses a method and system for determining proper reference electrode bias utilizing a dissolved oxygen (DO) probe, based on the result of a short duration test. The innovation described herein thus accommodates for the problems associated with earlier DO probes and techniques, as described earlier. In accordance with a preferred embodiment of the present invention, DO probe electronics can be configured for constant current operation, as opposed to the normal controlled potential mode.

Figure 5:
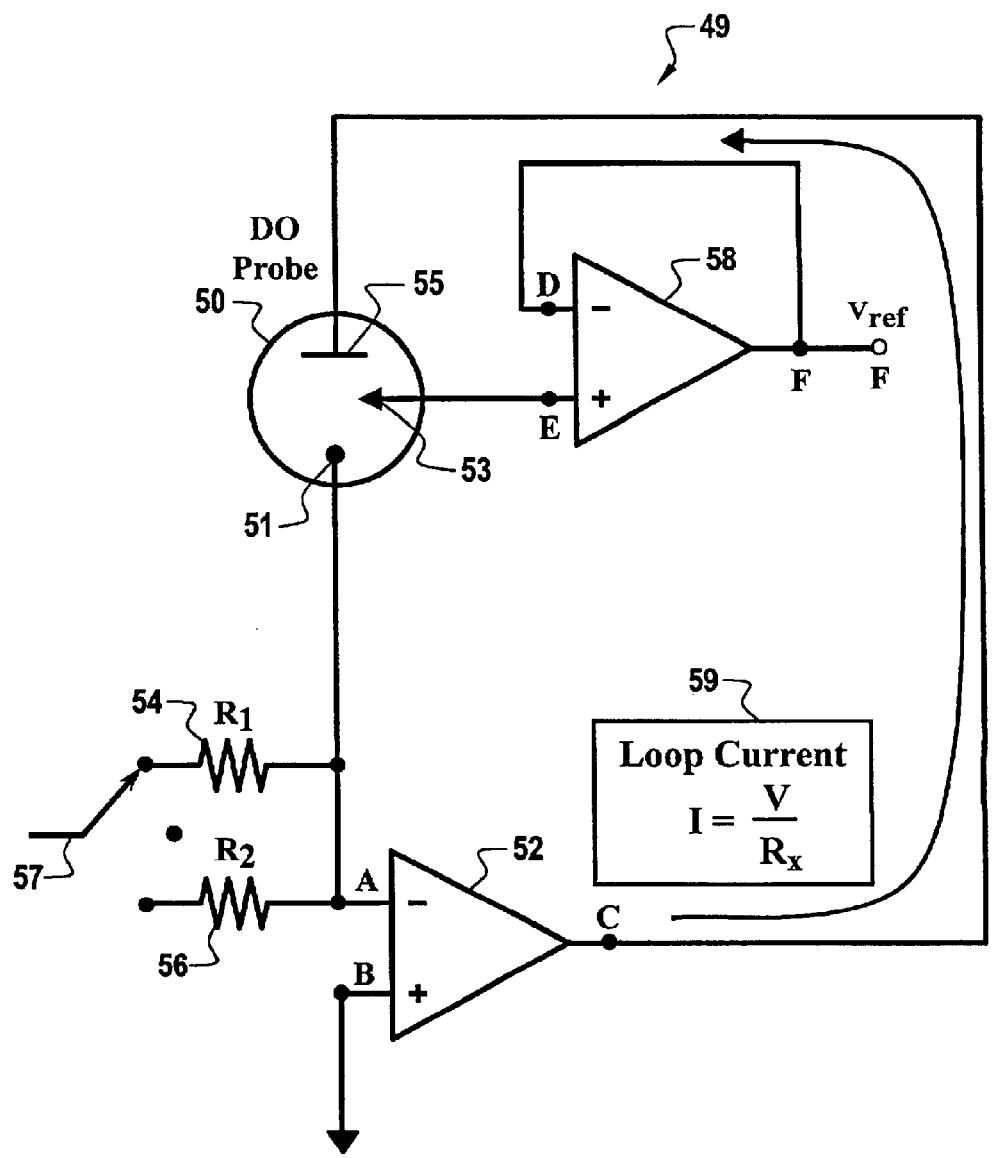
FIG. 5 depicts a schematic diagram of a DO probe in controlled current mode, in accordance with a preferred embodiment of the present invention.

FIG. 5 depicts a schematic diagram 49 of a DO probe 50 in a controlled current mode, in accordance with a preferred embodiment of the present invention. DO probe 50 generally includes a cathode 51, a reference electrode 53 and an anode 55. Cathode 51 generally comprises a working electrode, while anode 55 generally comprises a counter electrode. Schematic diagram 49 also illustrates two resistors 54 and 56, which are electrically in parallel with one another. Resistor 54 is labeled R1 and resistor 56 is labeled R2 in FIG. 5. At least one of the two resistors, 56 and/or 54, can be connected to at least one amplifier. In FIG. 5, for example, resistor 56 is connected to an input (i.e., a negative input) of amplifier 52 at node A. Note that the constant current level(s) can be established by the ratio of voltage to resistance. One or more constant current levels can be established by changing drive voltage 57 (e.g., V or −V) and/or input resistance.

A positive input of amplifier 52 is connected to ground at node B. At least one of the two resistors 54 and/or 56 is connected to cathode 51. In FIG. 5, both resistors 54 and 56 are connected to cathode 51 at node A. Additionally, an output of at least one amplifier can be connected to anode 55. In FIG. 5 the output of amplifier 52 (i.e., node C) is connected to anode 55. At least one amplifier may be configured as a transconductance amplifier. Thus, amplifier 52 is configured as a transconductance amplifier, which functions as a constant current source developing an $I=V/R_1$ or $I=V/R_2$ anode-to-cathode loop current. Note that as illustrated at block 59 in FIG. 5, the loop current can be generally represented by the following equation (3):

$$I = \frac{V}{R_x} \quad (3)$$

DO probe 50 thus can include at least one amplifier, such as, for example, amplifier 52, which provides a constant current source sufficient to place the oxygen probe in a constant current mode.

In FIG. 5, reference electrode 53 monitors cathode potential for cathode-anode operation in a constant current mode, thereby producing a reference electrode voltage $V_{ref}$ at node F. An amplifier 58 is connected to reference electrode 53 at node E, which comprises a positive input to amplifier 58. Node F, which comprises an output of amplifier 58, is tied to node D, which comprises a negative input of amplifier 58. The reference electrode voltage $V_{ref}$ can be measured at a first current level and at a second current level utilizing DO probe 50 and the associated electronics illustrated in schematic diagram 49 of FIG. 5, wherein the first and second current levels define limitations of oxygen electrochemistry.

Figure 2:
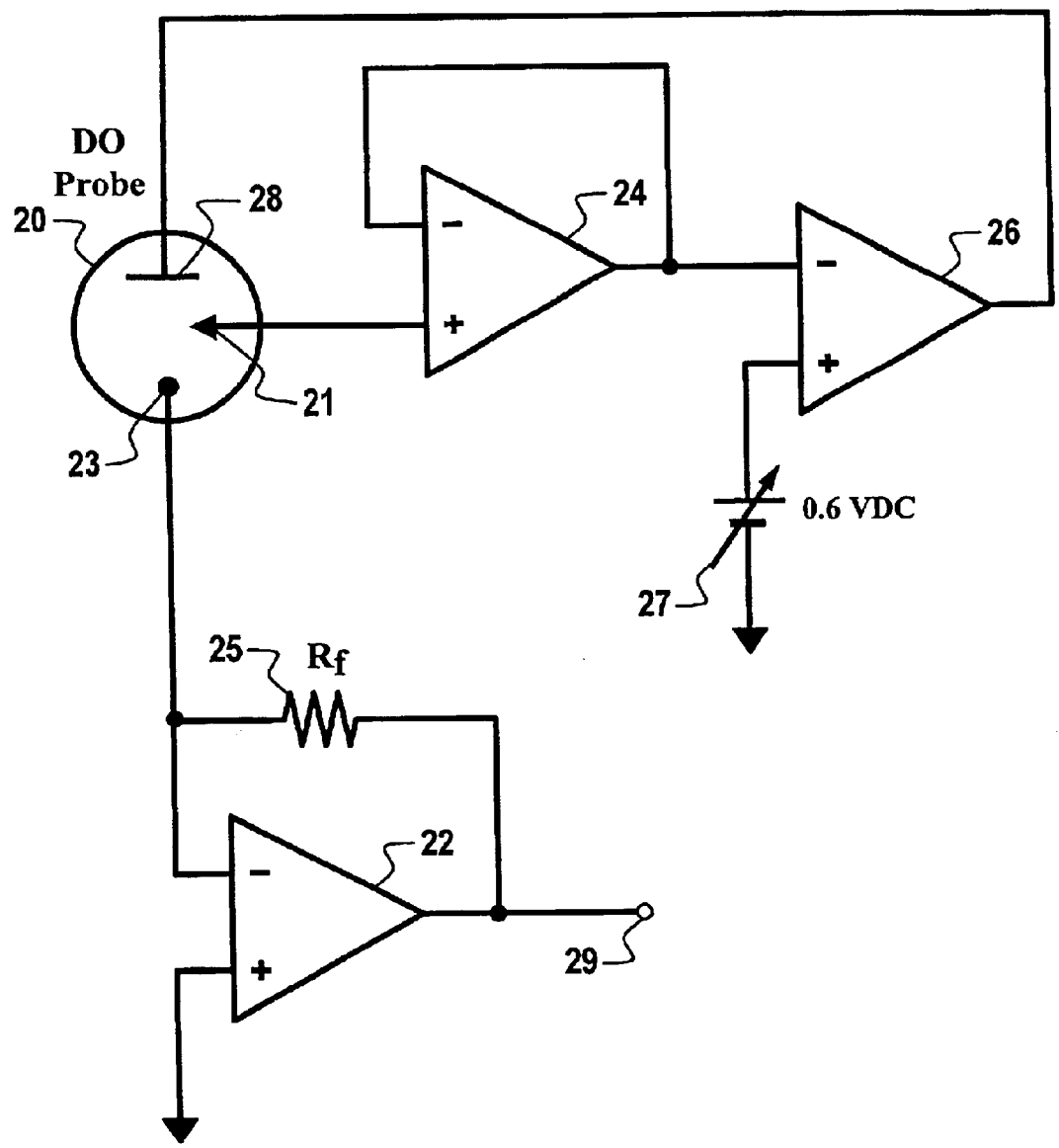
FIG. 2 illustrates a prior art schematic diagram illustrating a DO probe in controlled potential mode.

An optimum electrode bias voltage can then be calculated based on the reference electrode voltage $V_{ref}$ measured at the first current level and the second level to thereby provide accurate indications of dissolved oxygen thereof. Note that the optimum electrode bias can be calculated automatically, in response to measuring the reference electrode voltage at the first current level and at the second current level utilizing the DO probe. FIG. 5 thus generally illustrates a functional reconfiguration of the instrument electronics illustrated in FIG. 2 to allow for constant current operation. A reference electrode voltage follower (i.e., amplifier 58) can be utilized for measuring the potential of the reference electrode 53 versus a signal common or cathode potential. This measured voltage is labeled $V_{ref}$ as indicated at node F.

Figure 1:
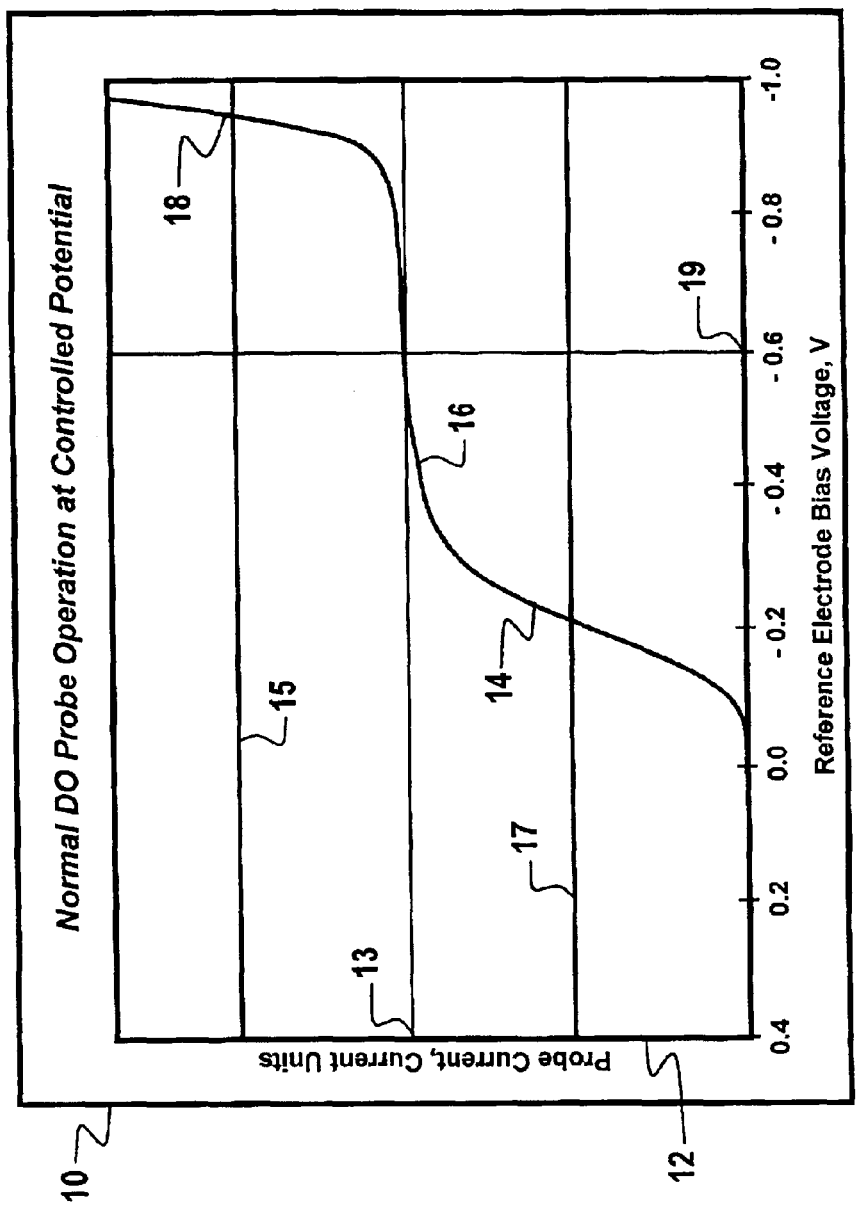
FIG. 1 depicts a prior art graph illustrating normal dissolved oxygen (DO) probe operation at a controlled potential.
Figure 3:
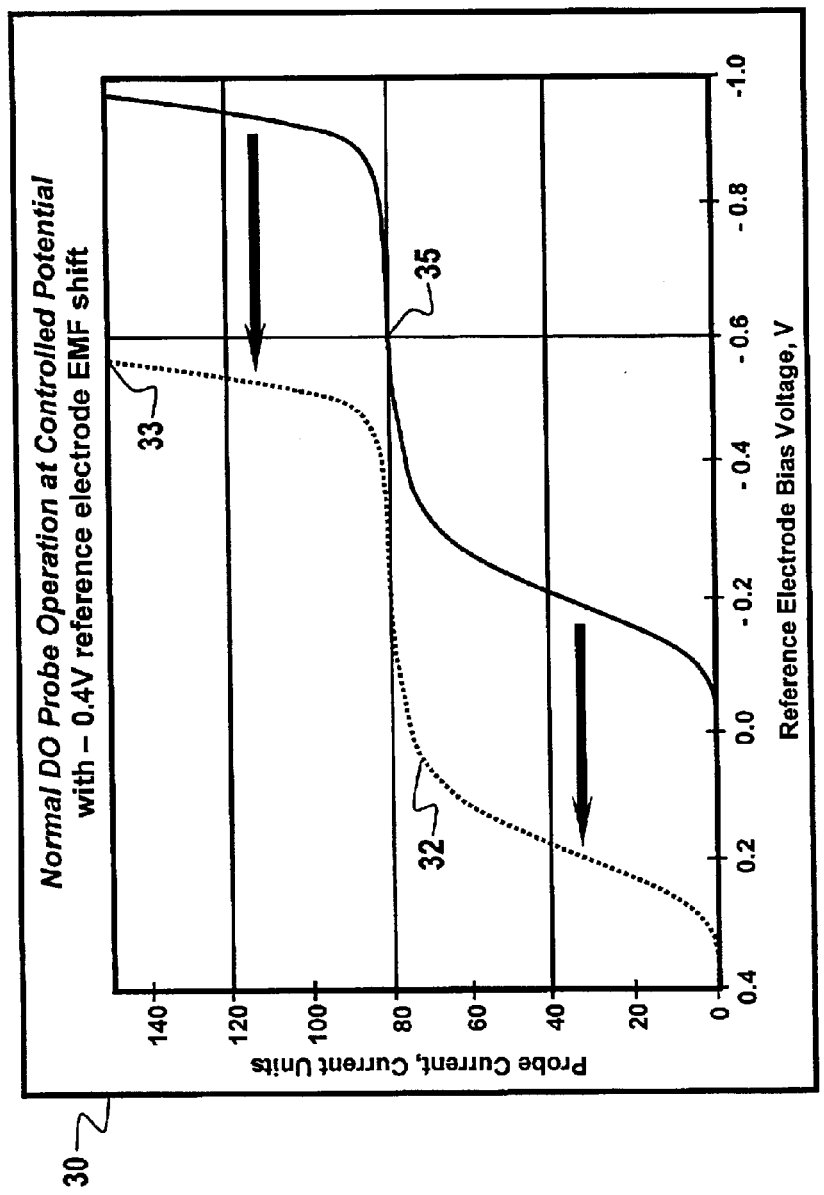
FIG. 3 depicts a prior art graph illustrating DO probe operation at a controlled potential with −0.4 V reference electrode EMF shift.
Figure 4:
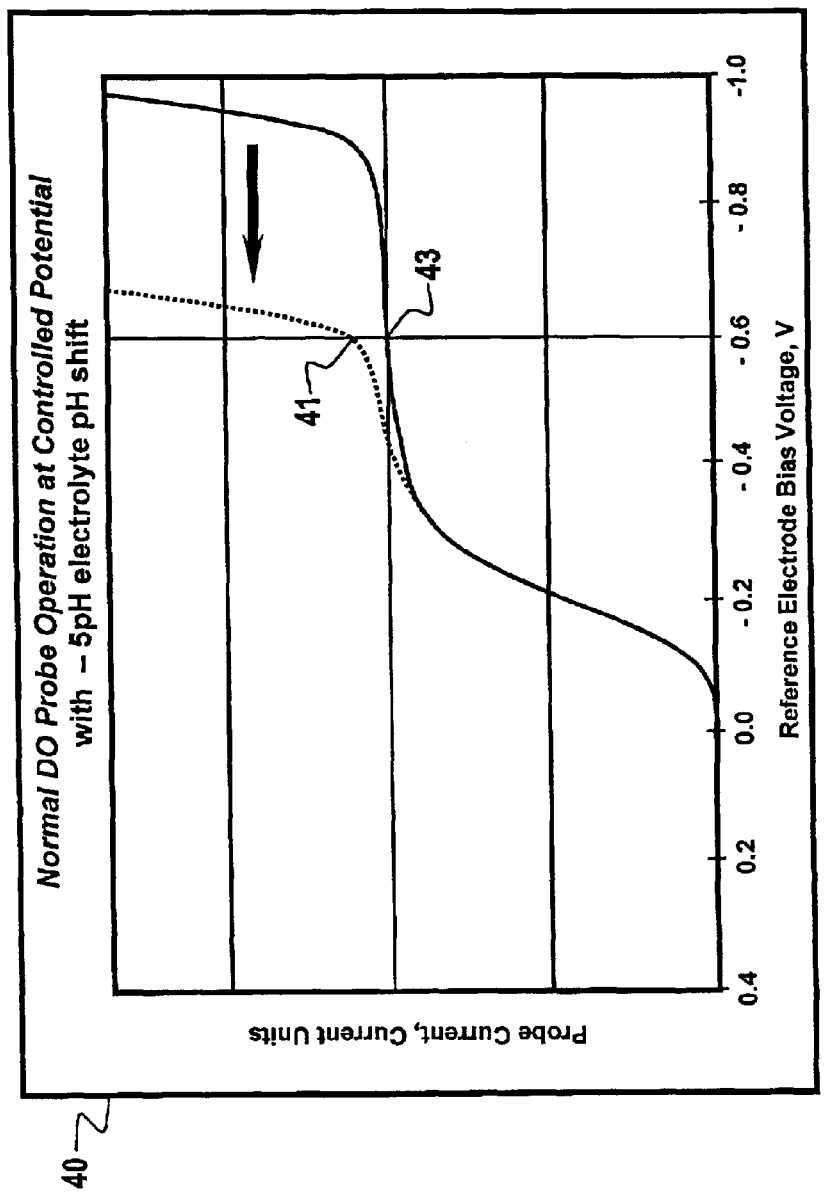
FIG. 4 illustrates a prior art graph illustrating DO probe operation at a controlled potential with a −5 pH electrolyte pH shift.

The current-voltage curves illustrated in FIGS. 1, 3 and 4 herein are generic. Because measured currents are a function of electrode geometry, specific engineering units of the current axes are not shown. For a DO probe of the Honeywell 7931 design, for example, operated in air, limiting plateau currents can be expected in the 40 $\mu$A to 120 $\mu$A current range. Namely, in air, a current less than 40 $\mu$A could be obtained for bias voltages on the leading edge of the oxygen wave, and currents greater than 120 $\mu$A can only be obtained in the water reduction region. Because the controlled potential operating bias lies between these extreme voltages, the determination of the bounds of the oxygen wave tells one where the wave is located and, therefore, provides a rational basis for probe bias selection.

Figure 6:
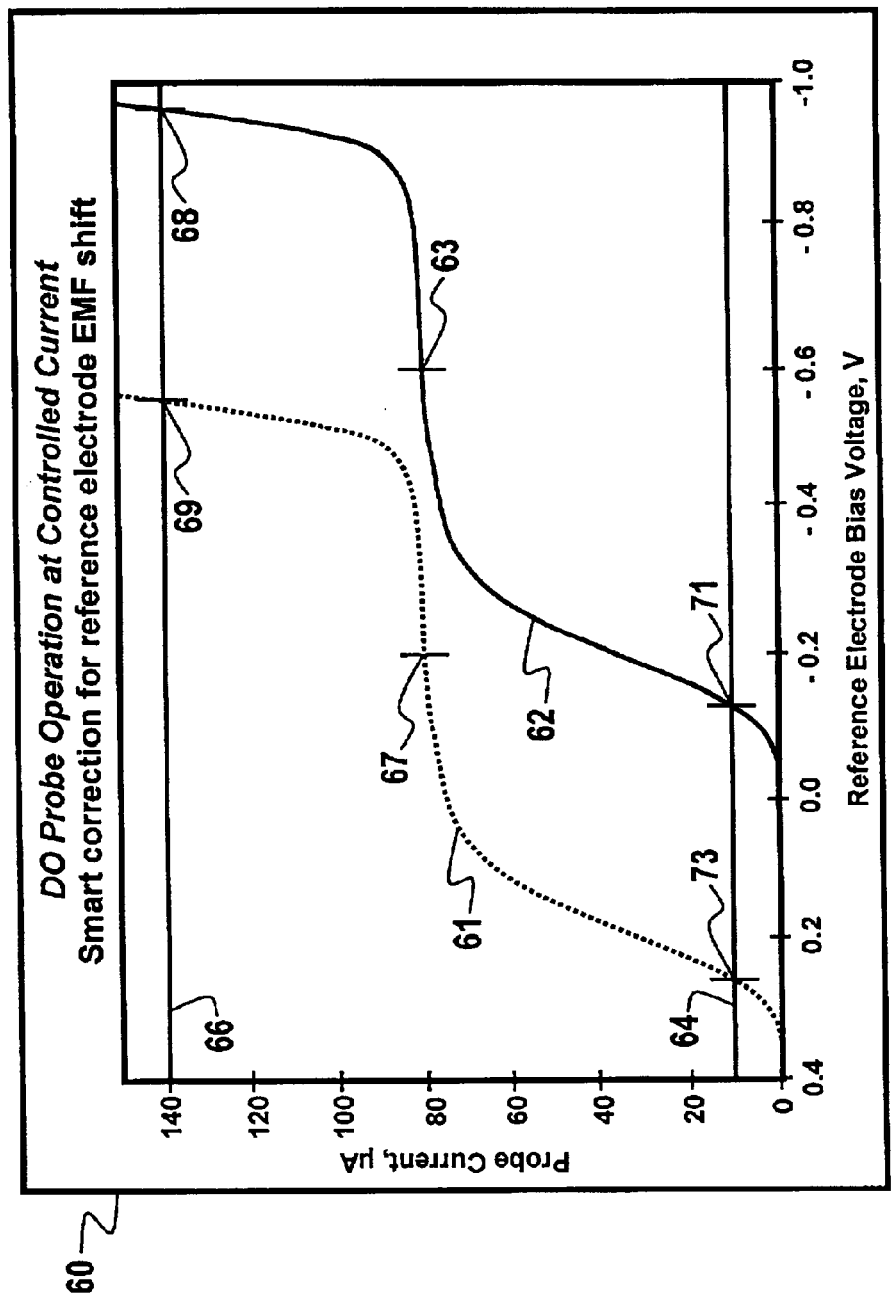
FIG. 6 illustrates a graph depicting a DO probe operation at a controlled current in which automatic corrections occur for reference electrode EMF, in accordance with a preferred embodiment of the present invention.

FIG. 6 illustrates a graph 60 illustrating a DO probe operation at a controlled current in which automatic corrections occur for reference electrode EMF shift, in accordance with a preferred embodiment of the present invention. FIG. 6 thus generally illustrates the current voltage curves of a nominal Honeywell 7931 DO probe before and after a 500 mV reference electrode shift. Note that the Honeywell 7931 DO probe is referred to herein for illustrative and edification purposes only and should not be interpreted by the reader as comprising a limiting feature of the present invention. The magnitude and direction of the shift is consistent with sulfide or mercaptan poisoning of the reference electrode described earlier (i.e., see discussion with respect to FIGS. 1 to 4).

The solid curve 62 illustrated in FIG. 6 to the right of the dotted curve 61 represents the "before" case. Dotted curve 61 located to the left of the solid curve 62 in FIG. 6 represents the "after" reference shift case. It should be noted that a significant error is obtained for probe operation at the old operating bias for the reference-shifted case. The present invention, on the other hand, can rapidly address this problem by determining the limits of the oxygen reduction wave and calculating a new operating point.

If the DO probe electronics are reconfigured for constant current operation, as functionally illustrated in FIG. 5, the voltage window of the reduction wave can be determined by measuring voltage for current values that are: 1) known to be a small fraction of the limiting current; and 2) known to exceed the limiting current value. For illustrative purposes only, an assumption is made that the ambient temperature limiting current of DO probe in air is 80 $\mu$A with specification limits of ±40 $\mu$A. Namely, DO probe currents below 40 $\mu$A or exceeding 120 $\mu$A are not expected for a functioning DO probe.

As illustrated, for example, a 10 $\mu$A constant current (i.e., current 64 in FIG. 6) can define the foot of the wave. Likewise, a 140 $\mu$A current (e.g., see current 66 in FIG. 6) defines the potential of water reduction, namely beyond the oxygen reduction wave. In constant current mode, reference electrode voltages can be measured both at the 10 $\mu$A and 140 $\mu$A levels by measuring $-V_{ref}$ at $I=V/R_1$ or $I=V/R_2$. The optimum operating point is thus clearly located between these measured voltages and, in the example illustrated in FIG. 6, the $-0.6V$ reference electrode bias point is 56% between the 10 $\mu$A and 140 $\mu$A-$V_{ref}$ voltages. Once these two voltages are determined, optimum bias and the electronics of the DO probe can be reconfigured for constant potential operation at the calculated bias. The probe is now functioning as a normal DO probe.

Note that in FIG. 6, the old operating bias before the reference electrode shift is indicated at point 63. The new operating bias after the reference electrode shift is indicated at point 67. Additionally, a "shifted" high reference voltage value is generally $-0.564$ V, while a "normal" high reference voltage value is generally $-8.964$ V. Thus, as is generally indicated at point 69, $-V_{ref}=-0.564$ V. As illustrated at point 68, $-V_{ref}=-0.964$ V. A shifted low reference voltage value is generally 0.265 V and a "normal" low reference voltage value is generally $-0.134$ V. As generally indicated at point 73, $-V_{ref}=+0.265$ V, and at point 71, $-V_{ref}=-0.134$ V.

It should be understood by those skilled in the art that oxygen solubility and diffusion coefficient are temperature dependent, resulting in a probe current temperature sensitivity. As a consequence, temperature-dependent high and low limit current thresholds can and should be selected with knowledge of probe temperature. As temperature is a usual companion measurement for conversion of oxygen partial pressure into concentration units, the effect of temperature on current-voltage characteristics can be readily accommodated.

Figure 7:
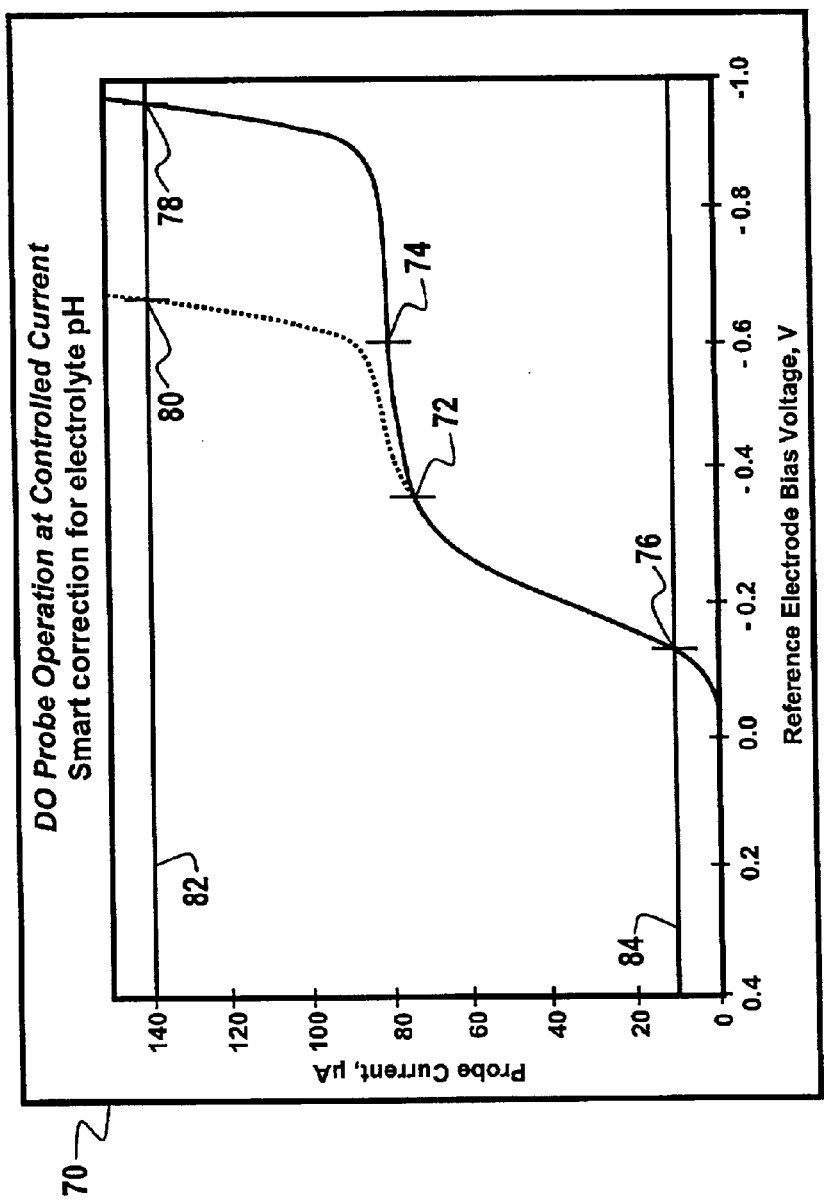
FIG. 7 depicts a graph illustrating a DO probe operation at a controlled current in which automatic corrections occur for electrolyte pH, in accordance with a preferred embodiment of the present invention.

FIG. 7 depicts a graph 70 illustrating a DO probe operation at a controlled current in which automatic corrections occur for electrolyte pH, in accordance with a preferred embodiment of the present invention. FIG. 7 illustrates the case for shift in electrolyte pH value. Baseline constant current operation results in the same high and low EMF limits resulting in a preferred $-0.6V$ bias. Following a 5-pH acidification of the electrolyte, the current voltage curve illustrates a higher signal and measurement error because of summation with water reduction currents.

Constant current operation at the foot of the dissolved oxygen reduction wave provides the same EMF value ($-V_{ref}=-0.134V$) because the pH does not have any effect on oxygen reduction. By contrast, the pH does have a dramatic effect on the high current EMF values, thereby reducing the water reduction potential from $-V_{ref}=-0.964V$ to $-V_{ref}=-0.664V$ as respectively indicated at points 78 and 80 in FIG. 7. Using the 56% rationale described above, the identification of the low and high current potentials ($-0.135V$ and $-0.664V$) can result in a calculated $-0.431V$ operating bias, near the center 72 of the remaining plateau. The old operating bias before the pH shift is indicated at point 74 in FIG. 7. Constant high current operation is illustrated in FIG. 7 by line 82, while constant low current operation is depicted by line 84.

The present invention can be implemented in the context of the electronic reconfiguration of a DO probe for constant current mode operation and acquisition of low and high current EMFs. The present invention can also be utilized to reconfigure a DO probe for the calculation of optimum bias, followed by electronic reconfiguration to a controlled potential mode, with a return to normal DO measurement.

The present invention thus discloses a method and system for determining dissolved oxygen. A constant current can be passed through a working electrode, such as, for example, cathode 51 illustrated in schematic diagram 49 of FIG. 5, at one or more predefined current levels to establish a reference electrode voltage relative to the working electrode. Note that while measurement of such a reference electrode voltage can take place at two current levels, measurement at a single current level, either high or low, may also be sufficient. The preferred order is: 1) dual-current reference electrode voltage measurement, 2) high current reference EMF measurement only and 3) low current reference measurement only. Thus, in a constant current mode of operation, the reference electrode voltage is measured at a first current level and at a second current level utilizing the oxygen probe, wherein the first and second current levels define limitations of oxygen electrochemistry. An optimum electrode bias voltage can thereafter be automatically calculated based the reference electrode voltage measured at the first current level and the second level to thereby provide accurate indications of dissolved oxygen thereof.

The oxygen probe can be configured to include at least one amplifier, which provides a constant current source sufficient to place the oxygen probe in the constant current mode. The amplifier may be, for example, a transconductance amplifier. The oxygen probe can be additionally configured to include at least two resistors electrically in parallel with another. At least one of the resistors is generally connected to an amplifier. The other of the two resistors can be coupled to a cathode. The output of the amplifier can be connected to an anode. At least one input of an amplifier can be connected to a reference electrode. The cathode generally comprises a working electrode. Thus, the constant current level(s) can be established by the ratio of voltage to resistance. One or more constant current levels can be established by changing drive voltage and/or input resistance.

The oxygen probe disclosed herein generally discloses a dissolved oxygen (DO) probe for measuring oxygen dissolved in a liquid. The present invention addresses problems associated with the momentary operation of an oxygen probe in a constant current mode, as opposed to a normal constant voltage mode. The reference electrode voltage is measured at two current levels, which define the limits of the oxygen electrochemistry. An optimum electrode bias can then be calculated and electronics associated with oxygen probe configured for normal DO measurement in a constant voltage mode.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only. Other variations and modifications of the present invention will be apparent to those of skill in the art, and it is the intent of the appended claims that such variations and modifications be covered. The description as set forth is not intended to be exhaustive or to limit the scope of the invention. Many modifications and variations are possible in light of the above teaching without departing from the scope of the following claims. It is contemplated that the use of the present invention can involve components having different characteristics. It is intended that the scope of the present invention be defined by the claims appended hereto, giving full cognizance to equivalents in all respects.

What is claimed is:

1. A method for determining dissolved oxygen utilizing an oxygen probe, said method comprising the steps of:
    passing a constant current though a working electrode to establish a reference electrode voltage relative to said working electrode;
    measuring said reference electrode voltage at a first current level and at a second current level utilizing said oxygen probe, wherein said first and second current levels define limitations of oxygen electrochemistry; and
    calculating an optimum electrode bias voltage based on said reference electrode voltage measured at said first current level and said second level to thereby indicate dissolved oxygen thereof.

2. The method of claim 1 wherein said constant current level comprises at least one predefined current level, wherein said at least one predefined current level is passed through said working electrode to establish said reference electrode voltage relative to said working electrode.

3. The method of claim 1 further comprising the step of:
    configuring said oxygen probe to include at least one amplifier, which provides a constant current source sufficient to place said oxygen probe in said constant current mode.

4. The method of claim 3 wherein said at least one amplifier comprises a transconductance amplifier.

5. The method of claim 1 further comprising the step of:
    configuring said oxygen probe to comprise at least two resistors electrically in parallel with another;
    connecting at least one of said at least two resistors to at least one amplifier;
    coupling at least one of said at least two resistors to a cathode;
    connecting an output of said at least one amplifier to an anode.

6. The method of claim 5 further comprising the step of:
    connecting an input of at least one amplifier to a reference electrode.

7. The method of claim 5 wherein said cathode comprises the working electrode.

8. The method of claim 1 further comprising the step of:
    determining said limitations of oxygen electrochemistry by determining limitations of an oxygen reduction wave measured utilizing said oxygen probe.

9. The method of claim 8 further comprising the step of:
    determining limitations of said oxygen reduction wave by compiling a voltage window of said oxygen reduction wave, wherein said voltage window is compiled based on measured voltage and current values known to be a fraction of a limiting current.

10. The method of claim 8 further comprising the step of:
    determining limitations of said oxygen reduction wave by compiling a voltage window of said oxygen reduction wave, wherein said voltage window is compiled based on measured voltage and current values known to exceed at least one limiting current value.

11. The method of claim 1 wherein said oxygen probe comprises a dissolved oxygen (DO) probe for measuring oxygen dissolved in a fluid.

12. The method of claim 1 wherein the step of calculating an optimum electrode bias voltage based on said reference electrode voltage measured at said first current level and said second level to thereby provide accurate indications of dissolved oxygen thereof, further comprises the step of:
    automatically calculating said optimum electrode bias, in response to measuring said reference electrode voltage at said first current level and at said second current level utilizing said oxygen probe.

13. The method of claim 1 further comprising the step of:
    configuring said oxygen probe and electronics associated therewith, such that said oxygen probe performs normal dissolved oxygen (DO) measurement in a constant voltage mode.

14. The method of claim 1 further comprising the step of:
    adjusting said constant current level to account for temperature effects associated with said dissolved oxygen probe and a constant current selection value.

15. The method of claim 1 further comprising the step of:
    maintaining said constant current level at a single current level.

16. A method for determining dissolved oxygen utilizing a dissolved oxygen probe, said method comprising the steps of:
    passing a constant current though a working electrode to establish a reference electrode voltage relative to said working electrode, wherein said constant current level comprises at least one predefined current level;
    measuring said reference electrode voltage at a first current level and at a second current level utilizing said dissolved oxygen probe, wherein said first and second current levels define limitations of oxygen electrochemistry; and calculating an optimum electrode bias voltage based on said reference electrode voltage measured at said first current level and said second level to thereby provide accurate indications of dissolved oxygen thereof;

configuring said dissolved oxygen probe to include at least one amplifier, which provides a constant current source sufficient to place said dissolved oxygen probe in said constant current mode, wherein said at least one amplifier comprises a transconductance amplifier; and adjusting said constant current level to account for temperature effects associated with said dissolved oxygen probe and a constant current selection value.

17. A system for determining dissolved oxygen utilizing an oxygen probe, said system comprising:

a current mechanism for passing a constant current though a working electrode to establish a reference electrode voltage relative to said working electrode;

a measurement mechanism for measuring said reference electrode voltage at a first current level and at a second current level utilizing said oxygen probe, wherein said first and second current levels define limitations of oxygen electrochemistry; and a calculating mechanism for calculating an optimum electrode bias voltage based on said reference electrode voltage measured at said first current level and said second level to thereby provide accurate indications of dissolved oxygen thereof.

18. The system of claim 17 wherein said constant current level comprises at least one predefined current level, wherein said at least one predefined current level is passed through said working electrode to establish said reference electrode voltage relative to said working electrode.

19. The system of claim 17 wherein said oxygen probe comprises at least one amplifier, which provides a constant current source sufficient to place said oxygen probe in said constant current mode.

20. The system of claim 19 wherein said at least one amplifier comprises a transconductance amplifier.

21. The system of claim 17 further comprising:

said oxygen probe comprising at least two resistors electrically in parallel with another;

at least one of said at least two resistors connected to at least one amplifier;

at least one of said at least two resistors coupled to a cathode; and an output of said at least one amplifier connected to an anode.

22. The system of claim 21 wherein an input of at least one amplifier is connected to a reference electrode.

23. The system of claim 21 wherein said cathode comprises the working electrode.

24. The system of claim 17 further comprising wherein said limitations of oxygen electrochemistry are determined by determining limitations of an oxygen reduction wave measured utilizing said oxygen probe.

25. The system of claim 24 wherein limitations of said oxygen reduction wave are determined by compiling a voltage window of said oxygen reduction wave, wherein said voltage window is compiled based on measured voltage and current values known to be a small fraction of a limiting current.

26. The system of claim 24 wherein said limitations of said oxygen reduction wave are determined by compiling a voltage window of said oxygen reduction wave, wherein said voltage window is compiled based on measured voltage and current values known to exceed at least one limiting current value.

27. The system of claim 17 wherein said oxygen probe comprises a dissolved oxygen (DO) probe for measuring oxygen dissolved in a fluid.

28. The system of claim 17 wherein said calculating mechanism further comprises:

a calculating mechanism for automatically calculating said optimum electrode bias, in response to measuring said reference electrode voltage at said first current level and at said second current level utilizing said oxygen probe.

29. The system of claim 17 wherein said oxygen probe and electronics associated therewith are configured such that said oxygen probe performs normal dissolved oxygen (DO) measurement in a constant voltage mode.

30. The system of claim 17 further comprising:

an adjusting said constant current level to account for temperature effects associated with said dissolved oxygen probe and a constant current selection value.

31. The system of claim 17 wherein said constant current level is maintained at a single current level.

32. A system for determining dissolved oxygen utilizing a dissolved oxygen probe, said system comprising:

a current device, wherein said current device passes a constant current though a working electrode to establish a reference electrode voltage relative to said working electrode, wherein said constant current level comprises at least one predefined current level;

a measuring device, wherein said measuring device measures said reference electrode voltage at a first current level and at a second current level utilizing said dissolved oxygen probe, wherein said first and second current levels define limitations of oxygen electrochemistry; and a calculating device, wherein said calculating device calculates an optimum electrode bias voltage based on said reference electrode voltage measured at said first current level and said second level to thereby provide accurate indications of dissolved oxygen thereof;

said dissolved oxygen probe comprising at least one amplifier, which provides a constant current source sufficient to place said dissolved oxygen probe in said constant current mode, wherein said at least one amplifier comprises a transconductance amplifier; and an adjusting mechanism for adjusting said constant current level to account for temperature effects associated with said dissolved oxygen probe and a constant current selection value.

* * * * *